(12) United States Patent
Bär et al.

(10) Patent No.: US 6,172,074 B1
(45) Date of Patent: Jan. 9, 2001

(54) IMIDAZOPYRIDINES AND OXAZOLOPYRIDINES

(75) Inventors: Thomas Bär; Wolf-Rüdiger Ulrich, both of Constance (DE)

(73) Assignee: Byk Gulden Lomberg Chemische Fabrik GmbH, Constance (DE)

( * ) Notice: Under 35 U.S.C. 154(b), the term of this patent shall be extended for 0 days.

(21) Appl. No.: 09/284,981

(22) PCT Filed: Nov. 5, 1997

(86) PCT No.: PCT/EP97/06130

§ 371 Date: May 10, 1999

§ 102(e) Date: May 10, 1999

(87) PCT Pub. No.: WO98/21209

PCT Pub. Date: May 22, 1998

(30) Foreign Application Priority Data

Nov. 11, 1996 (DE) ................................. 196 46 460
Nov. 13, 1996 (AT) ................................. 96118187

(51) Int. Cl.⁷ ................. A61K 31/4353; A61K 31/4355; C07D 491/10
(52) U.S. Cl. ............................ 514/278; 514/302; 546/15; 546/115
(58) Field of Search ....................... 546/15, 115; 514/278, 514/302

(56) References Cited

U.S. PATENT DOCUMENTS 4,038,396 * 7/1977 Shen et al. .......................... 424/256

FOREIGN PATENT DOCUMENTS

| 2330109 | * | 1/1974 | (DE) . |
| 2633905 | * | 2/1977 | (DE) . |
| 0079083 | * | 5/1983 | (EP) . |
| 94/12461 | * | 6/1994 | (WO) . |
| 95/14680 | * | 6/1994 | (WO) . |
| WO 96/11917 | | 4/1996 | (WO) ........................... C07D/263/57 |

* cited by examiner

*Primary Examiner*—Alan L. Rotman
*Assistant Examiner*—Rita Desai
(74) *Attorney, Agent, or Firm*—Jacobson, Price, Holman & Stern, PLLC

(57) ABSTRACT

Compounds of formula (I), wherein A, B, D, E, R1, R2, R3 and Y have the meanings cited in the description, are effective bronchial therapeutic agents.

8 Claims, No Drawings

IMIDAZOPYRIDINES AND OXAZOLOPYRIDINES

This is a § 371 of PCT/EP97/06130, filed Nov. 5, 1997, which claims the benefit of foreign priority document No. 196 46 460.9, filed in Germany on Nov. 11, 1996.

FIELD OF APPLICATION OF THE INVENTION

The invention relates to novel oxazolo- and imidazopyridines, which are used in the pharmaceutical industry for the production of medicaments.

KNOWN TECHNICAL BACKGROUND

German Patent Applications DE 23 30 109, DE 25 27 321, DE 26 19 547 and DE 26 33 905 and the American U.S. Pat. No. 4,038,396 describe 2-(substituted phenyl)-oxazolo[4,5-b]pyridines, -oxazolo[4,5-c]pyridines and -oxazolo[5,4-b]pyridines as antiinflammatory, antipyretic and analgesic compounds.

German Patent Application DE 23 61 757 describes 2-(substituted phenyl)-imidazo[4,5-b]pyridines having antihypertensive, positively inotropic, platelet aggregation-inhibiting and bleeding time-prolonging properties.

European Patent Application EP 022 495 describes 2-(substituted phenyl)-imidazo[4,5-b]pyridines as cardiotonic agents and hypertensive agents. European Patent Application EP 072 926 describes 2-(substituted phenyl)-imidazo[4,5-b]- and -[4,5-c]pyridines having positively inotropic properties. European Patent Application EP 079 083 describes 2-phenylimidazo[4,5-c]pyridines having vasodilating, positively inotropic and platelet aggregation-inhibiting properties, which have no inhibitory action on myocardial phosphodiesterase.

PCT Application WO94/12461 describes, inter alia, 2-(substituted phenyl)-imidazopyridines and -oxazolopyridines as selective inhibitors of phosphodiesterase of type 4.

DESCRIPTION OF THE INVENTION

It has now been found that the novel compounds of the general formula I described below in greater detail have surprising and particularly advantageous properties.

The invention thus relates to compounds of the formula I (I)

in which
of the group of symbols A, B, D and E, independently of one another, one symbol is N (nitrogen), one symbol is C—X and the remaining two symbols are C—H, where
X is hydrogen, hydroxyl, halogen, cyano, nitro, carboxyl, 1–4C-alkyl, 1–4C-alkylcarbonyl, 1–4C-alkylcarbonyloxy, 1–4C-alkoxy, 1–4C-alkoxycarbonyl, amino, mono- or di-1–4C-alkylamino, 1–4C-alkylcarbonylamino, hydroxy-1–4C-alkyl, hydroxysulfonyl, 1–4C-alkylsulfonyl, 1–4C-alkoxysulfonyl or sulfamoyl,
Y is O (oxygen) or NH,
R1 is 1–4C-alkoxy, 3–7C-cycloalkoxy, 3–7C-cycloalkylmethoxy, benzyloxy or 1–4C-alkoxy which is completely or predominantly substituted by fluorine,
R2 is hydrogen or 1–4C-alkyl and
R3 is hydrogen or 1–4C-alkyl,
or in which
R2 and R3, together and including the two carbon atoms to which they are bonded, are a spiro-linked 5-, 6- or 7-membered hydrocarbon ring, if desired interrupted by an oxygen atom,
and the salts and the N-oxides of these compounds.

Halogen within the meaning of the invention is fluorine, chlorine, bromine or iodine.

1–4C-Alkyl represents straight-chain or branched alkyl radicals having 1 to 4 carbon atoms. Examples which may be mentioned are the butyl, isobutyl, sec-butyl, tert-butyl, propyl, isopropyl, ethyl and methyl radicals.

1–4C-Alkylcarbonyl represents a carbonyl group to which one of the abovementioned 1–4C-alkyl radicals is bonded. An example which may be mentioned is the acetyl radical ($CH_3CO$—).

1–4C-Alkylcarbonyloxy radicals contain, in addition to the oxygen atom, one of the abovementioned 1–4C-alkylcarbonyl radicals. An example which may be mentioned is the acetoxy radical ($CH_3CO$—O—).

1–4C-Alkoxy represents a radical which, in addition to the oxygen atom, contains a straight-chain or branched alkyl radical having 1 to 4 carbon atoms. Examples of alkoxy radicals having 1 to 4 carbon atoms which may be mentioned are the butoxy, isobutoxy, sec-butoxy, tert-butoxy, propoxy, isopropoxy, ethoxy and methoxy radicals.

1–4C-Alkoxycarbonyl represents a carbonyl group to which one of the abovementioned 1–4C-alkoxy radicals is bonded. Examples which may be mentioned are the methoxycarbonyl radical ($CH_3O$—CO—) and the ethoxycarbonyl radical ($CH_3CH_2O$—CO—).

Examples of mono- or di-1–4C-alkylamino radicals which may be mentioned are the methylamino, dimethylamino and diethylamino radicals.

An example of a 1–4C-alkylcarbonylamino radical which may be mentioned is the acetylamino radical (—NH—CO—$CH_3$).

Hydroxy-1–4C-alkyl represents abovementioned 1–4C-alkyl radicals which are substituted by a hydroxyl group. Examples which may be mentioned are the hydroxyethyl and the hydroxymethyl radicals.

1–4C-Alkylsulfonyl represents a sulfonyl group to which one of the abovementioned 1–4C-alkyl radicals is bonded. An example which may be mentioned is the methylsulfonyl radical ($CH_3SO_2$—).

1–4C-Alkoxysulfonyl represents a sulfonyl group to which one of the abovementioned 1–4C-alkoxy radicals is bonded. Examples which may be mentioned are the methoxysulfonyl radical ($CH_3O$—$SO_2$—) and the ethoxysulfonyl radical ($CH_3CH_2O$—$SO_2$—).

3–7C-Cycloalkoxy represents the cyclopropyloxy, cyclobutyloxy, cyclopentyloxy, cyclohexyloxy and cycloheptyloxy radicals. The 3–5C-cycloalkoxy radicals cyclopropyloxy, cyclobutyloxy and cyclopentyloxy may preferably be mentioned.

3–7C-Cycloalkylmethoxy represents cyclopropylmethoxy, cyclobutylmethoxy, cyclopentylmethoxy, cyclohexylmethoxy and cycloheptylmethoxy. The 3–5C-cycloalkylmethoxy radicals cyclopropylmethoxy, cyclobutylmethoxy and cyclopentylmethoxy may preferably be mentioned.

Examples of 1–4C-alkoxy which is completely or predominantly substituted by fluorine are the 2,2,3,3,3-pentafluoropropoxy, perfluoroethoxy, 1,2,2-trifluoroethoxy and in particular the 1,1,2,2-tetrafluoroethoxy, 2,2,2-trifluoroethoxy, trifluoromethoxy and, preferably, the difluoromethoxy radicals.

A spiro-linked 5-, 6- or 7-membered hydrocarbon ring, if desired interrupted by an oxygen atom, which may be mentioned is the cyclopentane, cyclohexane, cycloheptane, tetrahydrofuran or tetrahydropyran ring.

Salts of compounds of the formula I—depending on substitution—are all acid addition salts or all salts with bases. Particular mention may be made of the pharmacologically tolerable salts of the inorganic and organic acids customarily used in pharmacy. Those suitable are, on the one hand, water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, where the acids are employed in salt preparation—depending on whether a mono- or polybasic acid is involved and depending on which salt is desired—in an equimolar quantitative ratio or one differing therefrom.

On the other hand, salts with bases are also suitable. Examples of salts with bases which may be mentioned are alkali metal (lithium, sodium, potassium) or calcium, aluminum, magnesium, titanium, ammonium, meglumine or guanidinium salts, where here too, the bases are employed in salt preparation in an equimolar quantitative ratio or one differing therefrom.

Pharmacologically intolerable salts which can initially be obtained, for example, as process products in the preparation of the compounds according to the invention on an industrial scale, are converted into pharmacologically tolerable salts by processes known to the person skilled in the art.

It is known to the person skilled in the art that the compounds according to the invention and their salts, if, for example, they are isolated in crystalline form, can contain various amounts of solvents. The invention therefore also comprises all solvates and in particular all hydrates of the compounds of the formula I, and all solvates and in particular all hydrates of the salts of the compounds of the formula I.

Compounds of the formula I to be emphasized are those in which
from the group of symbols A, B, D and E, independently of one another, one symbol is N (nitrogen), one symbol is C—X and the remaining two symbols are C—H, where
 X is hydrogen, hydroxyl, halogen, cyano, nitro, carboxyl, 1–4C-alkyl, 1–4C-alkylcarbonyloxy, 1–4C-alkoxy, 1–4C-alkoxycarbonyl, amino, mono- or di-1–4C-alkylamino, 1–4C-alkylcarbonylamino, hydroxy-1–4C-alkyl, hydroxysulfonyl or sulfamoyl,
 Y is O or NH,
 R1 is 1–4C-alkoxy, 3–7C-cycloalkoxy, 3–7C-cycloalkylmethoxy or 1–4C-alkoxy which is completely or predominantly substituted by fluorine,
 R2 is 1–4C-alkyl and
 R3 is hydrogen or 1–4C-alkyl,
or in which
 R2 and R3, together and including the two carbon atoms to which they are bonded, are a spiro-linked cyclopentane, cyclohexane, tetrahydrofuran or tetrahydropyran ring, and the salts of these compounds.

Compounds of the formula I particularly to be emphasized are those in which
from the group of symbols A, B, D and E, independently of one another, one symbol is N (nitrogen), one symbol is C—X and the remaining two symbols are C—H, where
 X is hydrogen, halogen, carboxyl or 1–4C-alkoxycarbonyl,
 Y is O or NH,
 R1 is methoxy, ethoxy, cyclopropylmethoxy or 1–2C-alkoxy which is completely or predominantly substituted by fluorine,
 R2 is 1–4C-alkyl and
 R3 is hydrogen or 1–4C-alkyl,
or in which
 R2 and R3, together and including the two carbon atoms to which they are bonded, are a spiro-linked cyclopentane or cyclohexane ring,
and the salts of these compounds.

Preferred compounds of the formula I are those in which
from the group of symbols A, B, D and E, independently of one another, one symbol is N (nitrogen), one symbol is C—X and the remaining two symbols are C—H, where
 X is hydrogen or halogen,
 Y is O or NH,
 R1 is methoxy and
 R2 and R3, together and including the two carbon atoms to which they are bonded, are a spiro-linked cyclopentane or cyclohexane ring,
and the salts of these compounds.

Exemplary compounds according to the invention are listed in the following tables:

TABLE 1

Compounds of the formula I with Y = O, A = N, B = CH, D = CH, E = CH and the following further substituent meanings:

| R1 | R2 | R3 |
|---|---|---|
| $OCH_3$ | $CH_3$ | H |
| $OC_2H_5$ | $CH_3$ | H |
| $OCH_2C_3H_5$ | $CH_3$ | H |
| $OCF_2H$ | $CH_3$ | H |
| $OCF_3$ | $CH_3$ | H |
| $OCH_2CF_3$ | $CH_3$ | H |
| $OCH_3$ | $C_2H_5$ | $CH_3$ |
| $OC_2H_5$ | $C_2H_5$ | $CH_3$ |
| $OCH_2C_3H_5$ | $C_2H_5$ | $CH_3$ |
| $OCF_2H$ | $C_2H_5$ | $CH_3$ |
| $OCF_3$ | $C_2H_5$ | $CH_3$ |
| $OCH_2CF_3$ | $C_2H_5$ | $CH_3$ |
| $OCH_3$ | $CH_2CH_2CH_2$ | |
| $OC_2H_5$ | $CH_2CH_2CH_2$ | |
| $OCH_2C_3H_5$ | $CH_2CH_2CH_2$ | |
| $OCF_2H$ | $CH_2CH_2CH_2$ | |
| $OCF_3$ | $CH_2CH_2CH_2$ | |
| $OCH_2CF_3$ | $CH_2CH_2CH_2$ | |
| $OCH_3$ | $CH_2CH_2CH_2CH_2$ | |
| $OC_2H_5$ | $CH_2CH_2CH_2CH_2$ | |
| $OCH_2C_3H_5$ | $CH_2CH_2CH_2CH_2$ | |
| $OCF_2H$ | $CH_2CH_2CH_2CH_2$ | |
| $OCF_3$ | $CH_2CH_2CH_2CH_2$ | |
| $OCH_2CF_3$ | $CH_2CH_2CH_2CH_2$ | |
| $OCH_3$ | $CH_2$—O—$CH_2$ | |
| $OC_2H_5$ | $CH_2$—O—$CH_2$ | |

TABLE 1-continued

Compounds of the formula I with Y = O, A = N, B = CH, D = CH, E = CH and the following further substituent meanings:

| R1 | R2 | R3 |
|---|---|---|
| $OCH_2C_3H_5$ | | $CH_2$—O—$CH_2$ |
| $OCF_2H$ | | $CH_2$—O—$CH_2$ |
| $OCF_3$ | | $CH_2$—O—$CH_2$ |
| $OCH_2CF_3$ | | $CH_2$—O—$CH_2$ |
| $OCH_3$ | | $CH_2CH_2$—O |
| $OC_2H_5$ | | $CH_2CH_2$—O |
| $OCH_2C_3H_5$ | | $CH_2CH_2$—O |
| $OCF_2H$ | | $CH_2CH_2$—O |
| $OCF_3$ | | $CH_2CH_2$—O |
| $OCH_2CF_3$ | | $CH_2CH_2$—O |
| $OCH_3$ | | $CH_2CH_2$—O—$CH_2$ |
| $OC_2H_5$ | | $CH_2CH_2$—O—$CH_2$ |
| $OCH_2C_3H_5$ | | $CH_2CH_2$—O—$CH_2$ |
| $OCF_2H$ | | $CH_2CH_2$—O—$CH_2$ |
| $OCF_3$ | | $CH_2CH_2$—O—$CH_2$ |
| $OCH_2CF_3$ | | $CH_2CH_2$—O—$CH_2$ |

TABLE 2

Compounds of the formula I with Y = O, A = CH, B = N, D = CH, E = CH and the following further substituent meanings:

| R1 | R2 | R3 |
|---|---|---|
| $OCH_3$ | $CH_3$ | H |
| $OC_2H_5$ | $CH_3$ | H |
| $OCH_2C_3H_5$ | $CH_3$ | H |
| $OCF_2H$ | $CH_3$ | H |
| $OCF_3$ | $CH_3$ | H |
| $OCH_2CF_3$ | $CH_3$ | H |
| $OCH_3$ | $C_2H_5$ | $CH_3$ |
| $OC_2H_5$ | $C_2H_5$ | $CH_3$ |
| $OCH_2C_3H_5$ | $C_2H_5$ | $CH_3$ |
| $OCF_2H$ | $C_2H_5$ | $CH_3$ |
| $OCF_3$ | $C_2H_5$ | $CH_3$ |
| $OCH_2CF_3$ | $C_2H_5$ | $CH_3$ |
| $OCH_3$ | | $CH_2CH_2CH_2$ |
| $OC_2H_5$ | | $CH_2CH_2CH_2$ |
| $OCH_2C_3H_5$ | | $CH_2CH_2CH_2$ |
| $OCF_2H$ | | $CH_2CH_2CH_2$ |
| $OCF_3$ | | $CH_2CH_2CH_2$ |
| $OCH_2CF_3$ | | $CH_2CH_2CH_2$ |
| $OCH_3$ | | $CH_2CH_2CH_2CH_2$ |
| $OC_2H_5$ | | $CH_2CH_2CH_2CH_2$ |
| $OCH_2C_3H_5$ | | $CH_2CH_2CH_2CH_2$ |
| $OCF_2H$ | | $CH_2CH_2CH_2CH_2$ |
| $OCF_3$ | | $CH_2CH_2CH_2CH_2$ |
| $OCH_2CF_3$ | | $CH_2CH_2CH_2CH_2$ |
| $OCH_3$ | | $CH_2$—O—$CH_2$ |
| $OC_2H_5$ | | $CH_2$—O—$CH_2$ |
| $OCH_2C_3H_5$ | | $CH_2$—O—$CH_2$ |
| $OCF_2H$ | | $CH_2$—O—$CH_2$ |
| $OCF_3$ | | $CH_2$—O—$CH_2$ |
| $OCH_2CF_3$ | | $CH_2$—O—$CH_2$ |
| $OCH_3$ | | $CH_2CH_2$—O |
| $OC_2H_5$ | | $CH_2CH_2$—O |
| $OCH_2C_3H_5$ | | $CH_2CH_2$—O |
| $OCF_2H$ | | $CH_2CH_2$—O |
| $OCF_3$ | | $CH_2CH_2$—O |
| $OCH_2CF_3$ | | $CH_2CH_2$—O |
| $OCH_3$ | | $CH_2CH_2$—O—$CH_2$ |
| $OC_2H_5$ | | $CH_2CH_2$—O—$CH_2$ |
| $OCH_2C_3H_5$ | | $CH_2CH_2$—O—$CH_2$ |
| $OCF_2H$ | | $CH_2CH_2$—O—$CH_2$ |
| $OCF_3$ | | $CH_2CH_2$—O—$CH_2$ |
| $OCH_2CF_3$ | | $CH_2CH_2$—O—$CH_2$ |

TABLE 3

Compounds of the formula I with Y = O, A = CH, B = CH, D = N, E = CH and the following further substituent meanings:

| R1 | R2 | R3 |
|---|---|---|
| $OCH_3$ | $CH_3$ | H |
| $OC_2H_5$ | $CH_3$ | H |
| $OCH_2C_3H_5$ | $CH_3$ | H |
| $OCF_2H$ | $CH_3$ | H |
| $OCF_3$ | $CH_3$ | H |
| $OCH_2CF_3$ | $CH_3$ | H |
| $OCH_3$ | $C_2H_5$ | $CH_3$ |
| $OC_2H_5$ | $C_2H_5$ | $CH_3$ |
| $OCH_2C_3H_5$ | $C_2H_5$ | $CH_3$ |
| $OCF_2H$ | $C_2H_5$ | $CH_3$ |
| $OCF_3$ | $C_2H_5$ | $CH_3$ |
| $OCH_2CF_3$ | $C_2H_5$ | $CH_3$ |
| $OCH_3$ | | $CH_2CH_2CH_2$ |
| $OC_2H_5$ | | $CH_2CH_2CH_2$ |
| $OCH_2C_3H_5$ | | $CH_2CH_2CH_2$ |
| $OCF_2H$ | | $CH_2CH_2CH_2$ |
| $OCF_3$ | | $CH_2CH_2CH_2$ |
| $OCH_2CF_3$ | | $CH_2CH_2CH_2$ |
| $OCH_3$ | | $CH_2CH_2CH_2CH_2$ |
| $OC_2H_5$ | | $CH_2CH_2CH_2CH_2$ |
| $OCH_2C_3H_5$ | | $CH_2CH_2CH_2CH_2$ |
| $OCF_2H$ | | $CH_2CH_2CH_2CH_2$ |
| $OCF_3$ | | $CH_2CH_2CH_2CH_2$ |
| $OCH_2CF_3$ | | $CH_2CH_2CH_2CH_2$ |
| $OCH_3$ | | $CH_2$—O—$CH_2$ |
| $OC_2H_5$ | | $CH_2$—O—$CH_2$ |
| $OCH_2C_3H_5$ | | $CH_2$—O—$CH_2$ |
| $OCF_2H$ | | $CH_2$—O—$CH_2$ |
| $OCF_3$ | | $CH_2$—O—$CH_2$ |
| $OCH_2CF_3$ | | $CH_2$—O—$CH_2$ |
| $OCH_3$ | | $CH_2CH_2$—O |
| $OC_2H_5$ | | $CH_2CH_2$—O |
| $OCH_2C_3H_5$ | | $CH_2CH_2$—O |
| $OCF_2H$ | | $CH_2CH_2$—O |
| $OCF_3$ | | $CH_2CH_2$—O |
| $OCH_2CF_3$ | | $CH_2CH_2$—O |
| $OCH_3$ | | $CH_2CH_2$—O—$CH_2$ |
| $OC_2H_5$ | | $CH_2CH_2$—O—$CH_2$ |
| $OCH_2C_3H_5$ | | $CH_2CH_2$—O—$CH_2$ |
| $OCF_2H$ | | $CH_2CH_2$—O—$CH_2$ |
| $OCF_3$ | | $CH_2CH_2$—O—$CH_2$ |
| $OCH_2CF_3$ | | $CH_2CH_2$—O—$CH_2$ |

TABLE 4

Compounds of the formula I with Y = O, A = CH, B = CH, D = CH, E = N and the following further substituent meanings:

| R1 | R2 | R3 |
|---|---|---|
| $OCH_3$ | $CH_3$ | H |
| $OC_2H_5$ | $CH_3$ | H |
| $OCH_2C_3H_5$ | $CH_3$ | H |
| $OCF_2H$ | $CH_3$ | H |
| $OCF_3$ | $CH_3$ | H |
| $OCH_2CF_3$ | $CH_3$ | H |
| $OCH_3$ | $C_2H_5$ | $CH_3$ |
| $OC_2H_5$ | $C_2H_5$ | $CH_3$ |
| $OCH_2C_3H_5$ | $C_2H_5$ | $CH_3$ |
| $OCF_2H$ | $C_2H_5$ | $CH_3$ |
| $OCF_3$ | $C_2H_5$ | $CH_3$ |
| $OCH_2CF_3$ | $C_2H_5$ | $CH_3$ |
| $OCH_3$ | | $CH_2CH_2CH_2$ |
| $OC_2H_5$ | | $CH_2CH_2CH_2$ |
| $OCH_2C_3H_5$ | | $CH_2CH_2CH_2$ |
| $OCF_2H$ | | $CH_2CH_2CH_2$ |
| $OCF_3$ | | $CH_2CH_2CH_2$ |
| $OCH_2CF_3$ | | $CH_2CH_2CH_2$ |
| $OCH_3$ | | $CH_2CH_2CH_2CH_2$ |
| $OC_2H_5$ | | $CH_2CH_2CH_2CH_2$ |
| $OCH_2C_3H_5$ | | $CH_2CH_2CH_2CH_2$ |

TABLE 4-continued

Compounds of the formula I with Y = O, A = CH, B = CH, D = CH, E = N and the following further substituent meanings:

| R1 | R2 | R3 |
|---|---|---|
| $OCF_2H$ | | $CH_2CH_2CH_2CH_2$ |
| $OCF_3$ | | $CH_2CH_2CH_2CH_2$ |
| $OCH_2CF_3$ | | $CH_2CH_2CH_2CH_2$ |
| $OCH_3$ | | $CH_2-O-CH_2$ |
| $OC_2H_5$ | | $CH_2-O-CH_2$ |
| $OCH_2C_3H_5$ | | $CH_2-O-CH_2$ |
| $OCF_2H$ | | $CH_2-O-CH_2$ |
| $OCF_3$ | | $CH_2-O-CH_2$ |
| $OCH_2CF_3$ | | $CH_2-O-CH_2$ |
| $OCH_3$ | | $CH_2CH_2-O$ |
| $OC_2H_5$ | | $CH_2CH_2-O$ |
| $OCH_2C_3H_5$ | | $CH_2CH_2-O$ |
| $OCF_2H$ | | $CH_2CH_2-O$ |
| $OCF_3$ | | $CH_2CH_2-O$ |
| $OCH_2CF_3$ | | $CH_2CH_2-O$ |
| $OCH_3$ | | $CH_2CH_2-O-CH_2$ |
| $OC_2H_5$ | | $CH_2CH_2-O-CH_2$ |
| $OCH_2C_3H_5$ | | $CH_2CH_2-O-CH_2$ |
| $OCF_2H$ | | $CH_2CH_2-O-CH_2$ |
| $OCF_3$ | | $CH_2CH_2-O-CH_2$ |
| $OCH_2CF_3$ | | $CH_2CH_2-O-CH_2$ |

TABLE 5

Compounds of the formula I with Y = NH, A = N, B = CH, D = CH, E = CH and the following further substituent meanings:

| R1 | R2 | R3 |
|---|---|---|
| $OCH_3$ | $CH_3$ | H |
| $OC_2H_5$ | $CH_3$ | H |
| $OCH_2C_3H_5$ | $CH_3$ | H |
| $OCF_2H$ | $CH_3$ | H |
| $OCF_3$ | $CH_3$ | H |
| $OCH_2CF_3$ | $CH_3$ | H |
| $OCH_3$ | $C_2H_5$ | $CH_3$ |
| $OC_2H_5$ | $C_2H_5$ | $CH_3$ |
| $OCH_2C_3H_5$ | $C_2H_5$ | $CH_3$ |
| $OCF_2H$ | $C_2H_5$ | $CH_3$ |
| $OCF_3$ | $C_2H_5$ | $CH_3$ |
| $OCH_2CF_3$ | $C_2H_5$ | $CH_3$ |
| $OCH_3$ | | $CH_2CH_2CH_2$ |
| $OC_2H_5$ | | $CH_2CH_2CH_2$ |
| $OCH_2C_3H_5$ | | $CH_2CH_2CH_2$ |
| $OCF_2H$ | | $CH_2CH_2CH_2$ |
| $OCF_3$ | | $CH_2CH_2CH_2$ |
| $OCH_2CF_3$ | | $CH_2CH_2CH_2$ |
| $OCH_3$ | | $CH_2CH_2CH_2CH_2$ |
| $OC_2H_5$ | | $CH_2CH_2CH_2CH_2$ |
| $OCH_2C_3H_5$ | | $CH_2CH_2CH_2CH_2$ |
| $OCF_2H$ | | $CH_2CH_2CH_2CH_2$ |
| $OCF_3$ | | $CH_2CH_2CH_2CH_2$ |
| $OCH_2CF_3$ | | $CH_2CH_2CH_2CH_2$ |
| $OCH_3$ | | $CH_2-O-CH_2$ |
| $OC_2H_5$ | | $CH_2-O-CH_2$ |
| $OCH_2C_3H_5$ | | $CH_2-O-CH_2$ |
| $OCF_2H$ | | $CH_2-O-CH_2$ |
| $OCF_3$ | | $CH_2-O-CH_2$ |
| $OCH_2CF_3$ | | $CH_2-O-CH_2$ |
| $OCH_3$ | | $CH_2CH_2-O$ |
| $OC_2H_5$ | | $CH_2CH_2-O$ |
| $OCH_2C_3H_5$ | | $CH_2CH_2-O$ |
| $OCF_2H$ | | $CH_2CH_2-O$ |
| $OCF_3$ | | $CH_2CH_2-O$ |
| $OCH_2CF_3$ | | $CH_2CH_2-O$ |
| $OCH_3$ | | $CH_2CH_2-O-CH_2$ |
| $OC_2H_5$ | | $CH_2CH_2-O-CH_2$ |
| $OCH_2C_3H_5$ | | $CH_2CH_2-O-CH_2$ |
| $OCF_2H$ | | $CH_2CH_2-O-CH_2$ |

TABLE 5-continued

Compounds of the formula I with Y = NH, A = N, B = CH, D = CH, E = CH and the following further substituent meanings:

| R1 | R2 | R3 |
|---|---|---|
| $OCF_3$ | | $CH_2CH_2-O-CH_2$ |
| $OCH_2CF_3$ | | $CH_2CH_2-O-CH_2$ |

TABLE 6

Compounds of the formula I with Y = NH, A = CH, B = N, D = CH, E = CH and the following further substituent meanings:

| R1 | R2 | R3 |
|---|---|---|
| $OCH_3$ | $CH_3$ | H |
| $OC_2H_5$ | $CH_3$ | H |
| $OCH_2C_3H_5$ | $CH_3$ | H |
| $OCF_2H$ | $CH_3$ | H |
| $OCF_3$ | $CH_3$ | H |
| $OCH_2CF_3$ | $CH_3$ | H |
| $OCH_3$ | $C_2H_5$ | $CH_3$ |
| $OC_2H_5$ | $C_2H_5$ | $CH_3$ |
| $OCH_2C_3H_5$ | $C_2H_5$ | $CH_3$ |
| $OCF_2H$ | $C_2H_5$ | $CH_3$ |
| $OCF_3$ | $C_2H_5$ | $CH_3$ |
| $OCH_2CF_3$ | $C_2H_5$ | $CH_3$ |
| $OCH_3$ | | $CH_2CH_2CH_2$ |
| $OC_2H_5$ | | $CH_2CH_2CH_2$ |
| $OCH_2C_3H_5$ | | $CH_2CH_2CH_2$ |
| $OCF_2H$ | | $CH_2CH_2CH_2$ |
| $OCF_3$ | | $CH_2CH_2CH_2$ |
| $OCH_2CF_3$ | | $CH_2CH_2CH_2$ |
| $OCH_3$ | | $CH_2CH_2CH_2CH_2$ |
| $OC_2H_5$ | | $CH_2CH_2CH_2CH_2$ |
| $OCH_2C_3H_5$ | | $CH_2CH_2CH_2CH_2$ |
| $OCF_2H$ | | $CH_2CH_2CH_2CH_2$ |
| $OCF_3$ | | $CH_2CH_2CH_2CH_2$ |
| $OCH_2CF_3$ | | $CH_2CH_2CH_2CH_2$ |
| $OCH_3$ | | $CH_2-O-CH_2$ |
| $OC_2H_5$ | | $CH_2-O-CH_2$ |
| $OCH_2C_3H_5$ | | $CH_2-O-CH_2$ |
| $OCF_2H$ | | $CH_2-O-CH_2$ |
| $OCF_3$ | | $CH_2-O-CH_2$ |
| $OCH_2CF_3$ | | $CH_2-O-CH_2$ |
| $OCH_3$ | | $CH_2CH_2-O$ |
| $OC_2H_5$ | | $CH_2CH_2-O$ |
| $OCH_2C_3H_5$ | | $CH_2CH_2-O$ |
| $OCF_2H$ | | $CH_2CH_2-O$ |
| $OCF_3$ | | $CH_2CH_2-O$ |
| $OCH_2CF_3$ | | $CH_2CH_2-O$ |
| $OCH_3$ | | $CH_2CH_2-O-CH_2$ |
| $OC_2H_5$ | | $CH_2CH_2-O-CH_2$ |
| $OCH_2C_3H_5$ | | $CH_2CH_2-O-CH_2$ |
| $OCF_2H$ | | $CH_2CH_2-O-CH_2$ |
| $OCF_3$ | | $CH_2CH_2-O-CH_2$ |
| $OCH_2CF_3$ | | $CH_2CH_2-O-CH_2$ |

TABLE 7

Compounds of the formula I with Y = NH, A = CCl, B = N, D = CH, E = CH and the following further substituent meanings:

| R1 | R2 | R3 |
|---|---|---|
| $OCH_3$ | $CH_3$ | H |
| $OC_2H_5$ | $CH_3$ | H |
| $OCH_2C_3H_5$ | $CH_3$ | H |
| $OCF_2H$ | $CH_3$ | H |
| $OCF_3$ | $CH_3$ | H |
| $OCH_2CF_3$ | $CH_3$ | H |
| $OCH_3$ | $C_2H_5$ | $CH_3$ |
| $OC_2H_5$ | $C_2H_5$ | $CH_3$ |
| $OCH_2C_3H_5$ | $C_2H_5$ | $CH_3$ |

TABLE 7-continued

Compounds of the formula I with Y = NH, A = CCl, B = N, D = CH, E = CH and the following further substituent meanings:

| R1 | R2 | R3 |
|---|---|---|
| $OCF_2H$ | $C_2H_5$ | $CH_3$ |
| $CF_3$ | $C_2H_5$ | $CH_3$ |
| $OCH_2CF_3$ | $C_2H_5$ | $CH_3$ |
| $OCH_3$ | | $CH_2CH_2CH_2$ |
| $OC_2H_5$ | | $CH_2CH_2CH_2$ |
| $OCH_2C_3H_5$ | | $CH_2CH_2CH_2$ |
| $OCF_2H$ | | $CH_2CH_2CH_2$ |
| $OCF_3$ | | $CH_2CH_2CH_2$ |
| $OCH_2CF_3$ | | $CH_2CH_2CH_2$ |
| $OCH_3$ | | $CH_2CH_2CH_2CH_2$ |
| $OC_2H_5$ | | $CH_2CH_2CH_2CH_2$ |
| $OCH_2C_3H_5$ | | $CH_2CH_2CH_2CH_2$ |
| $OCF_2H$ | | $CH_2CH_2CH_2CH_2$ |
| $OCF_3$ | | $CH_2CH_2CH_2CH_2$ |
| $OCH_2CF_3$ | | $CH_2CH_2CH_2CH_2$ |
| $OCH_3$ | | $CH_2$—O—$CH_2$ |
| $OC_2H_5$ | | $CH_2$—O—$CH_2$ |
| $OCH_2C_3H_5$ | | $CH_2$—O—$CH_2$ |
| $OCF_2H$ | | $CH_2$—O—$CH_2$ |
| $OCF_3$ | | $CH_2$—O—$CH_2$ |
| $OCH_2CF_3$ | | $CH_2$—O—$CH_2$ |
| $OCH_3$ | | $CH_2CH_2$—O |
| $OC_2H_5$ | | $CH_2CH_2$—O |
| $OCH_2C_3H_5$ | | $CH_2CH_2$—O |
| $OCF_2H$ | | $CH_2CH_2$—O |
| $OCF_3$ | | $CH_2CH_2$—O |
| $OCH_2CF_3$ | | $CH_2CH_2$—O |
| $OCH_3$ | | $CH_2CH_2$—O—$CH_2$ |
| $OC_2H_5$ | | $CH_2CH_2$—O—$CH_2$ |
| $OCH_2C_3H_5$ | | $CH_2CH_2$—O—$CH_2$ |
| $OCF_2H$ | | $CH_2CH_2$—O—$CH_2$ |
| $OCF_3$ | | $CH_2CH_2$—O—$CH_2$ |
| $OCH_2CF_3$ | | $CH_2CH_2$—O—$CH_2$ | and salts of the compounds mentioned in the tables.

The compound of the formula I if Y is NH, can be tautomers and—if the substituents —R2 and —$CH_2R3$ are not identical—chiral compounds. The invention therefore comprises both the pure tautomers and enantiomers and their mixtures in any mixing ratio, including the racemates. The enantiomers can be separated in a manner known per se (for example by preparation and separation of appropriate diastereoisomeric compounds).

Preferred compounds of the formula I, however, are those in which the substituents —R2 and —$CH_2R3$ are identical or in which R2 and R3, together and including the two carbon atoms to which they are bonded, are a spiro-linked 5-, 6- or 7-membered hydrocarbon ring, if desired interrupted by an oxygen atom.

The invention further relates to processes for the preparation of the compounds of the formula I and their salts. The first process (cf. scheme 1) comprises reacting compounds of the formula II in which R1, R2 and R3 have the meanings indicated above and Z is a suitable leaving group with compounds of the formula III in which Y is O (oxygen) or NH, and A, B, D and E have the meanings indicated above.

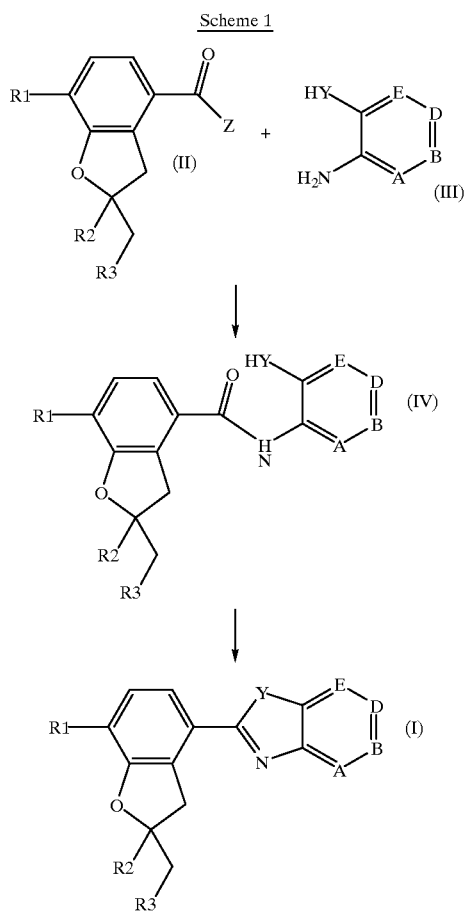

Scheme 1

The leaving groups Z which are suitable are familiar to the person skilled in the art on the basis of his expert knowledge. For example, suitable acid halides of the formula II (Z=Cl or Br) are used as starting materials.

The reaction is preferably carried out in the presence of a base such as, for example, pyridine or triethylamine, in a suitable inert solvent, e.g. in a cyclic hydrocarbon such as toluene or xylene, or another inert solvent such as dioxane or without further solvents, preferably at elevated temperature.

The compounds of the formula IV first formed in the reaction, in which R1, R2, R3, A, B, D, E and Y have the meanings indicated above, are reacted by means of internal condensation to give corresponding compounds of the formula I. This internal condensation is preferably carried out in the presence of a suitable condensing agent, such as thionyl chloride or phosphorus oxychloride, in a suitable inert solvent or without further solvent, using an excess of condensing agent, preferably at elevated temperature, in particular at the boiling temperature of the solvent or condensing agent used.

The reaction is carried out, for example, as described in the following examples, or in a manner familiar per se to the person skilled in the art (e.g. as described in German Patent Application DE 23 30 109, in American U.S. Pat. No, 4,038,396, in J. Med. Chem. 1978, 21, (11), 1159 ff., in European Patent Application EP 072 926, in J. Med. Chem. 1985, 28 (6), 717–727 or in Arch. Pharm. 1990, 323, (8), 501–505).

The compounds of the formula I obtained can then be converted into their salts and, if appropriate, salts of the compounds of formula I obtained can be converted into free compounds.

If desired, compounds of the formula I obtained can also be converted into the corresponding N-oxides.

The N-oxidation is carried out in a manner likewise familiar to the person skilled in the art, e.g. with the aid of m-chloroperoxybenzoic acid in dichloromethane at room temperature. The reaction conditions which are specifically necessary for carrying out the process are known to the person skilled in the art on the basis of his expert knowledge.

Compounds of the formula II in which Z is a suitable leaving group and R1, R2 and R3 have the meanings indicated above can be prepared from the corresponding compounds of the formula II, in which Z is a hydroxyl group and R1, R2 and R3 have the meanings indicated above, as described in the following examples or in a manner familiar per se to the person skilled in the art.

Compounds of the formula II in which Z is a hydroxyl group and R1, R2 and R3 have the meanings indicated above can be obtained as described in WO 96/03399 or by methods and techniques familiar to the person skilled in the art.

Compounds of the formula III are known or can be prepared using customary processes in a manner familiar per se to the person skilled in the art.

The second process (cf. scheme 2) differs from the first process in that in the last reaction step the pyridine ring is synthesized, and not the imidazolo or the oxazolo ring as described in the first process.

The process comprises reacting compounds of the formula V

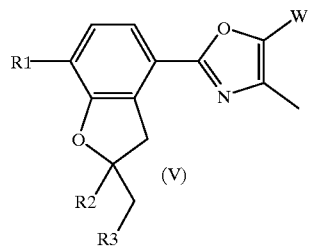

in which R1, R2 and R3 have the meanings indicated above and W is CHO, with compounds of the formula $N_3CH_2COOR$, where R is 1–4C-alkyl.

The reaction is carried out in two steps in a manner known per se to the person skilled in the art, for example as described in the examples. In the first step, the aldehyde group of the compounds of the formula V (W=CHO) is condensed with the $CH_2$ group of the α-azidoester ($N_3CH_2COOR$) in the presence of a suitable base such as, for example, NaOR (R=1–4C-alkyl). In the second step, the (oxazolo)pyridine ring closure is carried out by thermal treatment in an inert solvent, such as, for example, xylene.

Scheme 2

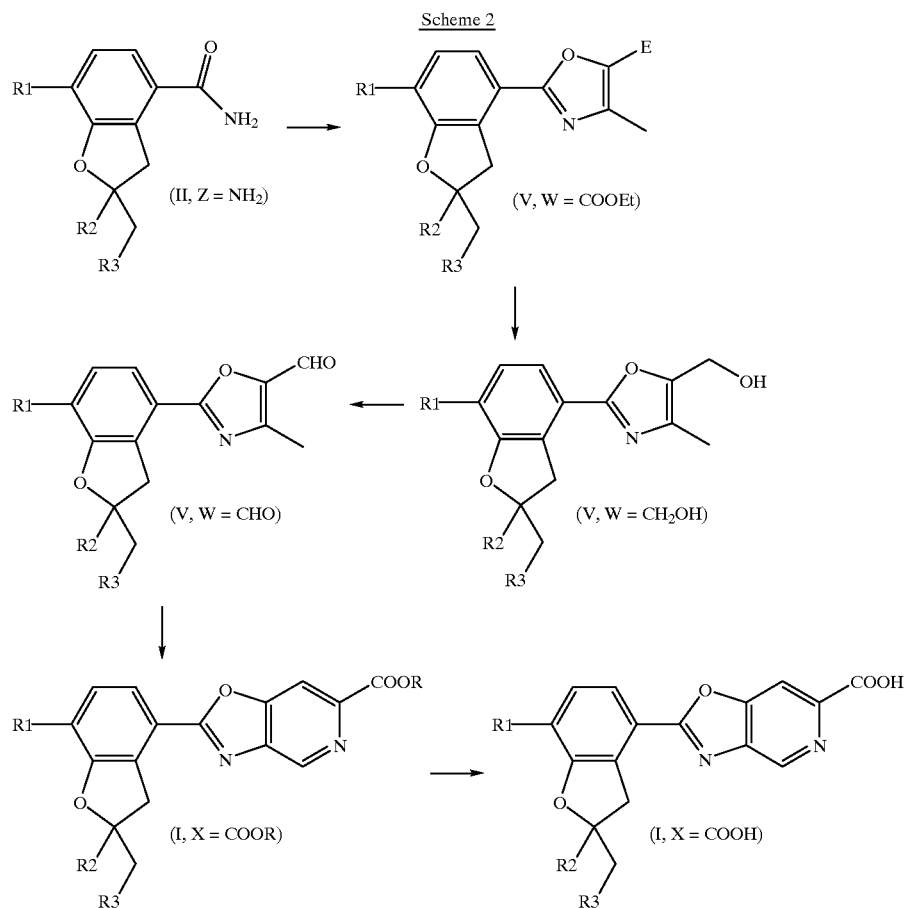

The process is particularly suitable for the preparation of oxazolo[4,5-c]pyridine compounds which have an ester or carboxyl group in the 6-position.

If desired, compounds of the formula I in which R1, R2 and R3 have the meanings indicated above and X is COOR can be converted into the corresponding carboxylic acids of the formula I by use of methods known to the person skilled in the art, for example by hydrolysis.

Compounds of the formula $N_3CH_2COOR$ are known or can be prepared in a manner familiar per se to the person skilled in the art using customary processes.

Compounds of the formula V in which R1, R2 and R3 have the meanings indicated above and W is CHO can be prepared from the corresponding compounds of the formula V in which W is COOEt by the combination of a reduction with an oxidation reaction (W=COOEt→W=CH$_2$OH→W=CHO).

Compounds of the formula V in which R1, R2 and R3 have the meanings indicated above and W is COOEt can be prepared from the corresponding compounds of the formula II in which Z is NH$_2$(amino) by reaction with, for example, ethyl 2-chloroacetoacetate.

Compounds of the formula II in which R1, R2 and R3 have the meanings indicated above and Z is NH$_2$ (amino) can be prepared from the corresponding compounds of the formula II in which Z is a suitable leaving group, for example a halogen atom, by reaction with ammonia.

The substances according to the invention are isolated and purified in a manner known per se, for example by distilling off the solvent in vacuo and recrystallizing the resulting residue from a suitable solvent or subjecting it to one of the customary purification methods, such as, for example, column chromatography on suitable support material.

Salts are obtained by dissolving the free compounds in a suitable solvent, e.g. in a chlorinated hydrocarbon, such as methylene chloride or chloroform, or a low molecular weight aliphatic alcohol (ethanol, isopropanol) which contains the desired acid or base, or to which the desired acid or base is then added. The salts are obtained by filtering, reprecipitating, precipitating with a nonsolvent for the addition salt or by evaporating the solvent. The salts obtained can be converted by alkalization or by acidification into the free compounds, which can in turn be converted into salts. In this manner, pharmacologically intolerable salts can be converted into pharmacologically tolerable salts.

The following examples serve to illustrate the invention in greater detail without restricting it. Further compounds of the formula I whose preparation is not described explicitly can also be prepared in an analogous manner or in a manner familiar per se to the person skilled in the art using customary process techniques.

In the examples, m.p. stands for melting point, b.p. for boiling point, h for hour(s), RT for room temperature, EF for empirical formula and MW for molecular weight. The compounds mentioned in the examples and their salts are a preferred subject of the invention.

EXAMPLES

Final Products 1. 2-(2,3-Dihydro-7-methoxybenzofuran-2-spiro-1'-cyclopentan-4-yl)oxazolo[4,5-b]pyridine 500 mg (1.5 mmol) of N-(3-hydroxypyridin-2-yl)-2,3-dihydro-7-methoxybenzofuran-2-spiro-1'-cyclopentane-4-carboxamide are stirred at 70° C. for 3 h in 2 ml of SOCl$_2$. Excess SOCl$_2$ is removed by distillation and the residue is chromatographed on silica gel. The title compound is obtained by crystallization from diethyl ether. M.p. 171° C.

2. 2-(2,3-Dihydro-7-methoxybenzofuran-2-spiro-1'-cyclopentan-4-yl)oxazolo[5,4-b]pyridine 880 mg (2.6 mmol) of N-(2-hydroxypyridin-3-yl)-2,3-dihydro-7-methoxybenzofuran-2-spiro-1'-cyclopentane-4-carboxamide are stirred at 80° C. for 16 h in 5 ml of SOCl$_2$. Excess SOCl$_2$ is distilled off and the residue is chromatographed using a 9:1 mixture of toluene and ethyl acetate. The title compound is obtained by crystallization from diethyl ether. M.p. 140° C.

3. 2-(2,3-Dihydro-7-methoxybenzofuran-2-spiro-1'-cyclopentan-4-yl)oxazolo[4,5-c]pyridine 370 mg (1.1 mmol) of N-(4-hydroxypyridin-3-yl)-2,3-dihydro-7-methoxybenzofuran-2-spiro-1'-cyclopentane-4-carboxamide are stirred at 80° C. for 6 h in 3 ml of SOCl$_2$. Excess SOCl$_2$ is distilled off and the residue is purified by chromatography on silica gel using a 9:1 mixture of toluene and ethyl acetate. M.p. 158° C.

4. 2-(2,3-Dihydro-7-methoxybenzofuran-2-spiro-1'-cyclopentan-4-yl)imidazolo[4,5-c]pyridin The amide mixture obtained under starting material A4 is dissolved in 10 ml of POCl$_3$ and the solution is then stirred at 120° C. for 3 h. After cooling, it is poured onto ice water, adjusted to pH 8 using 10 N sodium hydroxide solution and extracted 3× with ethyl acetate. The combined extracts are dried over sodium sulfate and concentrated, and the residue is chromatographed on a silica gel column using ethyl acetate/methanol 9:1 as an eluent. The chromato-graphically pure fractions are combined and concentrated, and the residue is crystallized using petroleum ether. M.p. 197–200° C.

5. 2-(2,3-Dihydro-7-methoxybenzofuran-2-spiro-1'-cyclohexan-4-yl)imidazolo[4,5-c]pyridine Analogously to Example 4, the amide mixture obtained under starting material A5 is cyclized using POCl$_3$. The title compound is obtained after chromatography using ethyl acetate/methanol 95:5 and crystallization using petroleum ether. M.p. 183–185° C.

6. 2-(2,3-Dihydro-7-methoxybenzofuran-2-spiro-1'-cyclohexan-4-yl)imidazo[4,5-b]pyridine dihydrochloride hemihydrate Analogously to Example 4, the amide (1 g) obtained under starting material A6 is cyclized using POCl$_3$. After chromatography using ethyl acetate/methanol 6:4, the product is converted into the dihydrochloride using excess ethereal hydrochloric acid, dried in vacuo and crystallized using diisopropyl ether. M.p. 233–235° C.

7. 4-Chloro-2-(2,3-dihydro-7-methoxybenzofuran-2-spiro-1'-cyclopentan-4-yl)imidazo[4,5-c]pyridine Analogously to Example 4, the amide obtained under starting material A7 is cyclized using POCl$_3$. After chromatography on a silica gel column using ethyl acetate as an eluent, the title compound is crystallized from diethyl ether. M.p. 258–260° C.

8. Methyl 2-(2,3-dihydro-7-methoxybenzofuran-2-spiro-1'-cyclopentan-4-yl)oxazolo[4,5-c]pyridine-6-carboxylate 2.5 g (8 mmol) of 2-(2,3-dihydro-7-methoxybenzofuran-2-spiro-1'-cyclopentan-4-yl)-4-methyloxazole-5-carbaldehyde are suspended in 50 ml of methanol and treated with 5.7 ml of 30% strength sodium methanolate solution in methanol. 4.0 g (34 mmol) of methyl azidoacetate are added dropwise with ice-cooling and exclusion of light and the mixture is stirred at 10–15° C. for 1 h. The reaction mixture is then added to satd. ammonium chloride solution and extracted with dichloromethane. The phases are separated, the organic phase is concentrated and the residue is dried over MgSO$_4$. After removing the solvent by evaporation, the residue is washed by stirring in methanol and the intermediate compound is dried in a high vacuum. The dried azide is heated at 130° C. for 20 min in 100 ml of xylene. The xylene is evaporated in vacuo and the crude product is recrystallized in acetonitrile. 470 mg of the title compound of m.p. 194–195° C. are obtained.

9. 2-(2,3-Dihydro-7-methoxybenzofuran-2-spiro-1'-cyclopentan-4-yl)oxazolo[4,5-c]pyridine-6-carboxylic acid 400 mg (1 mmol) of methyl 2-(2,3-dihydro-7-methoxybenzofuran-2-spiro-1'-cyclopentan-4-yl)oxazolo[4,5-c]pyridine-6-carboxylate are hydrolyzed overnight at RT in 100 mg (4.0 mmol) of lithium hydroxide in 20 ml of a 1:1 mixture of methanol and water. The methanol is evaporated in vacuo, the reaction is treated with 20 ml of water and the mixture is acidified with 4 ml of 2N $H_2SO_4$. The crystal magma is washed with 50 ml of water and dried in a high vacuum. M.p. 200° C. (dec.).

Starting Materials

A1. N-(3-Hydroxypyridin-2-yl)-2,3-dihydro-7-methoxybenzofuran-2-spiro-1'-cyclopentane4-carboxamide 1.5 g (6.1 mmol) of 2,3-dihydro-7-methoxy-benzofuran-2-spiro-1'-cyclopentane-4-carboxylic acid are refluxed for 1.5 h with 6.1 g (51.3 mmol) of $SOCl_2$. Excess $SOCl_2$ is distilled off and the residue is freed from residual $SOCl_2$ by coevaporating with toluene a number of times. The acid chloride is dissolved in 50 ml of pyridine and treated with 680 mg (6.2 mmol) of 2-amino-3-hydroxypyridine. After 5 h at 80° C., the pyridine is removed by distillation and the residue is extracted from water using $CH_2Cl_2$. The dried organic phase is concentrated and the crude product is crystallized from diethyl ether. 1.08 g of the title compound are obtained. M.p. 162° C.

A2. N-(2-Hydroxypyridin-3-yl)-2,3-dihydro-7-methoxybenzofuran-2-spiro-1'-cyclopentane-4-carboxamide The title compound is obtained when 3-amino-2-hydroxypyridine is employed as a starting compound analogously to Example A1. M.p. 235–240° C.

A3. N-(4-Hydroxypyridin-3-yl)-2,3-dihydro-7-methoxybenzofuran-2-spiro-1'-cyclopentane--4-carboxamide The title compound is obtained when 3-amino-4-hydroxypyridine is employed as a starting compound analogously to Example A1.

A4. N-(4-Aminopyridin-3-yl)- and N-(3-aminopyridin-4-yl)-2,3-dihydro-7-methoxybenzofuran-2-spiro-1'-cyclopentane-4-carboxamide 1.8 g of 2,3-dihydro-7-methoxybenzofuran-2-spiro-1'-cyclopentane-4-carboxylic acid are dissolved in 50 ml of toluene and treated with 5 ml of $SOCl_2$ and the mixture is heated to boiling under reflux for 1 h. After cooling, the toluene is removed by distillation in a rotary evaporator, the residue is redistilled 2× with toluene to completely remove the excess $SOCl_2$ and the residue is dissolved in 20 ml of absolute dioxane. The solution is added dropwise with stirring at 40° C. to a solution of 1.1 g of 3,4-diaminopyridine and 1.3 ml of triethylamine in 100 ml of absolute dioxane. The mixture is stirred at 40° C. for a further 2 h, then poured onto water and extracted 3× with ethyl acetate. The combined extracts are dried over sodium sulfate and concentrated. The mixture of the title compounds thus obtained is reacted further without further purification.

A5. N-(4-Aminopyridin-3-yl)- and N-(3-aminopyridin4-yl)-2,3-dihydro-7-methoxybenzofuran-2-spiro-1'-cyclohexane4-carboxamide Analogously to starting material A4, the acid chloride is prepared from 2 g of 2,3-dihydro-7-methoxybenzofuran-2-spiro-1'-cyclohexane-4-carboxylic acid and reacted with 0.83 g of 3,4-diaminopyridine and 1.0 ml of triethylamine to give the acid amide mixture, which is reacted further without further purification.

A6. N-(2-Aminopyridin-3-yl)-2,3-dihydro-7-methoxybenzofuran-2-spiro-1'-cyclohexane-4-carboxamide Analogously to starting material A4, the acid chloride is prepared from 2 g of 2,3-dihydro-7-methoxybenzofuran-2-spiro-1'-cyclohexane-4-carboxylic acid and reacted with 0.83 g of 2,3-diaminopyridine and 1.0 ml of triethylamine to give the acid amide. The crude product is chromatographed on a silica gel column using ethyl acetate as an eluent. The chromatographically pure fractions are combined and concentrated. 1 g of the title compound is obtained as a yellow, viscous oil.

A7. N-(4-Amino-2-chloropyridin-3-yl)-2,3-dihydro-7-methxoybenzofuran-2-spiro-1'-cyclopentane-4-carboxamide Analogously to starting material A4, the acid chloride is prepared from 0.7 g of 2,3-dihydro-7-methoxybenzofuran-2-spiro-1'-cyclopentane-4-carboxylic acid and reacted with 0.4 g of 3,4-diamino-2-chloropyridine and 0.4 ml of triethylamine. The crude product is reacted further without further purification.

A8. 2-(2,3-Dihydro-7-methoxybenzofuran-2-spiro-1'-cyclopentan-4-yl)-4-methyloxazole-5-carbaldehyde 7.38 g (23 mmol) of 2-(2,3-dihydro-7-methoxybenzofuran-2-spiro-1'-cyclopentan-4-yl)-4-methyloxazol-5-ylmethanol are treated with 15 g of manganese dioxide in portions in 200 ml of dichloromethane at RT in the course of 24 h. The reaction mixture is filtered through kieselguhr, the filtrate is concentrated and the residue is crystallized from 2-propanol. 5.1 g of the title compound are obtained.

A9. 2-(2,3-Dihydro-7-methoxybenzofuran-2-spiro-1'-cyclopentan-4-yl)4-methyloxazol-5-ylmethanol 8.9 g (28 mmol) of ethyl 2-(2,3-dihydro-7-methoxybenzofuran-2-spiro-1'-cyclopentan-4-yl)-4-methyloxazole-5-carboxylate in 100 ml of THF are added dropwise at 60° C. to a suspension of 1.9 g (50 mmol) of $LiAlH_4$ in 40 ml of THF. After refluxing for 3 h, the mixture is slowly hydrolyzed with 10 ml of water, treated with 1.9 ml of 4N NaOH and filtered, and the organic phase of the filtrate is separated off, dried over $MgSO_4$ and concentrated. The residue is washed by stirring in petroleum ether. 6.6 g of the title compound are obtained.

A10. Ethyl 2-(2,3-dihydro-7-methoxybenzofuran-2-spiro-1'-cyclopentan-4-yl)-4-methyloxazole-5-carboxylate 15 g (61 mmol) of 2-(2,3-dihydro-7-methoxybenzofuran-2-spiro-1'-cyclopentan-4-yl)-4-benzamide are suspended in 25 ml (121 mmol) of 95% strength ethyl 2-chloroacetoacetate and 3.6 g (64 mmol) of calcium oxide are added in portions with stirring. The mixture is boiled for 4 days at 120° C. It is then treated with 15 ml of half-concentrated HCl, 300 ml of water and 100 ml of ethyl acetate. The phases are separated and the aqueous phase is extracted twice with 100 ml of ethyl acetate each time. The combined organic phases are dried ($MgSO_4$) and freed from the solvent. The residue is chromatographed on silica gel (toluene/ethyl acetate 40:1) and 6.9 g of the title compound are isolated.

A11. 2-(2,3-Dihydro-7-methoxybenzofuran-2-spiro-1'-cyclopentan-4-yl)-4-benzamide 3.5 g (14.0 mmol) of 2,3-dihydro-7-methoxy-benzofuran-2-spiro-1'-cyclopentan-4-ylcarboxylic acid are treated with 10 ml (about 140 mmol) of $SOCl_2$. The excess $SOCl_2$ is removed by distillation in vacuo and the residue is taken up in 20 ml of acetone. The mixture is treated with ice-cooling with 10 ml of conc. $NH_3$ and stirred for 1 h. The acetone is removed by distillation and the residue is partitioned between ethyl acetate and 0.5 N NaOH. The dried organic phase is crystallized from 5 ml of 50% strength methanol and 115 mg of the title compound of m.p. 149–151° C. are obtained.

COMMERCIAL UTILITY

The compounds according to the invention have valuable pharmacological properties which make them commercially utilizable. As selective cyclic nucleotide phosphodiesterase (PDE) inhibitors (namely of type 4), they are suitable, on the one hand, as bronchial therapeutics (for the treatment of airway obstructions on account of their dilating but also on account of their respiratory rate- or respiratory drive-increasing action) and for the elimination of erectile dysfunction on account of the vasodilating action, but on the other hand especially for the treatment of disorders, in particular of inflammatory nature, e.g. of the airways (asthma prophylaxis), of the skin, of the intestine, of the eyes, of the central nervous system and of the joints, which are mediated by mediators such as histamine, PAF (platelet-activating factor), arachidonic acid derivatives such as leukotrienes and prostaglandins, cytokines, interleukins, chemokines, alpha-, beta- and gamma-interferon, tumor necrosis factor (TNF) or oxygen radicals and proteases. The compounds according to the invention are distinguished here by low toxicity, good enteral absorption (high bioavailability), great therapeutic breadth and the absence of significant side effects.

On account of their PDE-inhibiting properties, the compounds according to the invention can be employed in human and veterinary medicine as therapeutics, where they can be used, for example, for the treatment and prophylaxis of the following diseases: acute and chronic (in particular inflammatory and allergen-induced) airway disorders of various origins (bronchitis, allergic bronchitis, bronchial asthma); dermatoses (especially of proliferative, inflammatory and allergic nature) such as psoriasis (vulgaris), toxic and allergic contact eczema, atopic eczema, seborrheic eczema, lichen simplex, sunburn, pruritus in the anogenital area, alopecia areata, hypertrophic scars, discoid lupus erythematosus, follicular and wide-area pyodermias, endogenous and exogenous acne, acne rosacea and other proliferative, inflammatory and allergic skin disorders; disorders which are based on an excessive release of TNF and leukotrienes, i.e. for example disorders of the arthritis type (rheumatoid arthritis, rheumatoid spondylitis, osteoarthritis and other arthritic conditions), disorders of the immune system (AIDS, multiple sclerosis), symptoms of shock [septic shock, endotoxin shock, gram-negative sepsis, toxic shock syndrome and ARDS (adult respiratory distress syndrome)] and generalized inflammations in the gastrointestinal area (Crohn's disease and ulcerative colitis); disorders which are based on allergic and/or chronic, faulty immunological reactions in the area of the upper airways (pharynx, nose) and the adjacent regions (paranasal sinuses, eyes), such as, for example, allergic rhinitis/sinusitis, chronic rhinitis/sinusitis, allergic conjunctivitis and nasal polyps; but also disorders of the heart which can be treated by PDE inhibitors, such as, for example, cardiac insufficiency, or disorders which can be treated on account of the tissue-relaxant action of the PDE inhibitors, such as, for example, erectile dysfunction or colics of the kidneys and the ureters in connection with kidney stones, or alternatively disorders of the CNS, such as, for example, depression or arteriosclerotic dementia.

A further subject of the invention is a process for the treatment of mammals, including man, which are suffering from one of the abovementioned diseases. The process comprises administering to the sick mammal a therapeutically efficacious and pharmacologically tolerable amount of one or more of the compounds according to the invention.

A further subject of the invention are the compounds according to the invention for use in the treatment and/or prophylaxis of the diseases mentioned.

The invention also relates to the use of the compounds according to the invention for the production of medicaments which are employed for the treatment and/or prophylaxis of the diseases mentioned.

Medicaments for the treatment and/or prophylaxis of the diseases mentioned and which contain one or more compounds according to the invention are furthermore a subject of the invention.

The medicaments are prepared by processes which are known per se and familiar to the person skilled in the art. As medicaments, the compounds according to the invention (=active compounds) are either employed as such, or preferably in combination with suitable pharmaceutical auxiliaries, e.g. in the form of tablets, coated tablets, capsules, suppositories, patches, emulsions, suspensions, gels or solutions, the active compound content advantageously being between 0.1 and 95%.

The person skilled in the art is familiar on the basis of his expert knowledge with auxiliaries which are suitable for the desired pharmaceutical formulations. In addition to solvents, gel-forming agents, ointment bases and other active compound carriers, it is possible to use, for example, antioxidants, dispersants, emulsifiers, preservatives, solubilizers or permeation promoters.

For the treatment of disorders of the respiratory tract, the compounds according to the invention are preferably also administered by inhalation. For this, these are either administered directly as a powder (preferably in micronized form) or by nebulization of solutions or suspensions which contain them. With respect to the preparations and administration forms, reference is made, for example, to the embodiments in European Patent 163 965.

For the treatment of dermatoses, the compounds according to the invention are in particular used in the form of those medicaments which are suitable for topical application. For the production of the medicaments, the compounds according to the invention (=active compounds) are preferably mixed with suitable pharmaceutical auxiliaries and processed to give suitable pharmaceutical formulations. Examples of suitable pharmaceutical formulations which may be mentioned are powders, emulsions, suspensions, sprays, oils, ointments, fatty ointments, creams, pastes, gels or solutions.

The pharmaceuticals according to the invention are prepared by processes known per se. The dosage of the active compounds is carried out in the order of magnitude customary for PDE inhibitors. Thus topical application forms (such as, for example, ointments) for the treatment of dermatoses contain the active compounds in a concentration of, for example, 0.1–99%. The dose for administration by inhalation is customarily between 0.01 and 1 mg per puff of spray. The customary dose in the case of systemic therapy (p.o. or i.v.) is between 0.1 and 200 mg per administration.

Biological Investigations

In the investigation of PDE4 inhibition at the cellular level, the activation of inflammatory cells is ascribed particular importance. An example which may be mentioned is the FMLP (N-formyl-methionylleucyl-phenylalanine)-induced superoxide production of neutrophilic granulocytes, which can be measured as luminol-potentiated chemoluminescence [McPhail L C, Strum S L, Leone P A and Sozzani S, The neutrophil respiratory burst mechanism. In "Immunology Series" 1992, 57, 47–76; ed. Coffey R G (Marcel Decker, Inc., New York-Basel-Hong Kong)].

Substances which inhibit chemoluminescence and cytokine secretion and the secretion of proinflammatory mediators on inflammatory cells, in particular neutrophilic and eosinophilic granulocytes, T lymphocytes, monocytes and macrophages, are those which inhibit PDE4. This isoenzyme of the phosphodiesterase families is particularly represented in granulocytes. Its inhibition leads to an increase in the intracellular cyclic AMP concentration and thus to the inhibition of cellular activation. PDE4 inhibition by the substances according to the invention is thus a central indicator of the suppression of inflammatory processes. (Giembycz M A, Could isoenzyme-selective phosphodiesterase inhibitors render bronchodilatory therapy redundant in the treatment of bronchial asthma? Biochem Pharmacol 1992, 43, 2041–2051; Trophy T J, et al., Phosphodiesterase inhibitors: new opportunities for treatment of asthma. Thorax 1991, 46, 512–523; Schudt C, et al., Zardaverine: a cyclic AMP PDE 3/4 inhibitor. In "New Drugs for Asthma Therapy", 379–402, Birkhäuser Verlag Basel 1991; Schudt C et al., Influence of selective phosphodiesterase inhibitors on human neutrophil functions and levels of cAMP and Ca; Naunyn-Schmiedebergs Arch Pharmacol 1991, 344, 682–690; Nielson C P et al., Effects of selective phosphodiesterase inhibitors on polymorphonuclear leukocyte respiratory burst. J. Allergy Clin Immunol 1990, 86, 801–808; Schade et al., The specific type 3 and 4 phosphodiesterase inhibitor zardaverine suppresses formation of tumor necrosis factor by macrophages. European Journal of Pharmacology 1993, 230, 9–14).

Inhibition of the PDE4 Activity

Methodology

The activity test was carried out according to the method of Bauer and Schwabe, which was adapted to microtiter plates (Naunyn-Schmiedeberg's Arch. Pharmacol. 1980, 311, 193–198). In this test, the PDE reaction is carried out in the first step. In a second step, the resulting 5'-nucleotide is cleaved by a 5'-nucleotidase of the snake venom from Crotalus atrox to give the uncharged nucleoside. In the third step, the nucleoside is separated from the residual charged substrate on ion-exchange columns. The columns are eluted directly into minivials, into which 2 ml of scintillator fluid are additionally added for counting, using 2 ml of 30 mM ammonium formate (pH 6.0).

The inhibitory values determined for the compounds according to the invention [inhibitory concentration as -log $IC_{50}$ (mol/l)] follow from Table A below, in which the numbers of the compounds correspond to the numbers of the examples.

TABLE A

| Inhibition of the PDE4 activity | |
|---|---|
| Compound | -log $IC_{50}$ |
| 1 | 7.93 |
| 2 | 6.61 |
| 3 | 8.76 |
| 4 | 8.08 |

TABLE A-continued

| Inhibition of the PDE4 activity | |
|---|---|
| Compound | -log $IC_{50}$ |
| 5 | 7.52 |
| 6 | 6.90 |
| 7 | 7.98 |

What is claimed is:
1. A compound of formula I

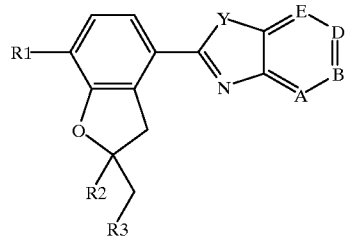

in which
of the group of symbols A, B, D and E, independently of one another, one symbol is N (nitrogen), one symbol is C—X and the remaining two symbols are C—H, where
X is hydrogen, hydroxyl, halogen, cyano, nitro, carboxyl, 1–4C-alkyl, 1–4C-alkylcarbonyl, 1–4C-alkylcarbonyloxy, 1–4C-alkoxy, 1–4C-alkoxycarbonyl, amino, mono- or di-1–4C-alkylamino, 1–4C-alkylcarbonylamino, hydroxy-1–4C-alkyl, hydroxysulfonyl, 1–4C-alkylsulfonyl, 1–4C-alkoxysulfonyl or sulfamoyl,
Y is O (oxygen),
R1 is 1–4C-alkoxy, 3–7C-cycloalkoxy, 3–7C-cycloalkylmethoxy, benzyloxy or 1–4C-alkoxy which is completely or predominantly substituted by fluorine, and
R2 and R3, together and including the two carbon atoms to which they are bonded, are a spiro-linked 5-, 6- or 7-membered hydrocarbon ring, if desired interrupted by an oxygen atom,
or a salt or N-oxide thereof.

2. A compound of formula I as claimed in claim 1, in which
from the group of symbols A, B, D and E, independently of one another, one symbol is N (nitrogen), one symbol is C—X and the remaining two symbols are C—H, where
X is hydrogen, hydroxyl, halogen, cyano, nitro, carboxyl, 1–4C-alkyl, 1–4C-alkylcarbonyloxy, 1–4C-alkoxy, 1–4C-alkoxycarbonyl, amino, mono- or di-1–4C-alkylamino, 1–4C-alkylcarbonylamino, hydroxy-1–4C-alkyl, hydroxysulfonyl or sulfamoyl,
Y is O,
R1 is 1–4C-alkoxy, 3–7C-cycloalkoxy, 3–7C-cycloalkylmethoxy or 1–4C-alkoxy which is completely or predominantly substituted by fluorine, and
R2 and R3, together and including the two carbon atoms to which they are bonded, are a spiro-linked cyclopentane, cyclohexane, tetrahydrofuran or tetrahydropyran ring,
or a salt thereof.

3. A compound of formula I as claimed in claim 1, in which from the group of symbols A, B, D and E, independently of one another, one symbol is N (nitrogen), one symbol is C—X and the remaining two symbols are C—H, where X is hydrogen, halogen, carboxyl or 1–4C-alkoxycarbonyl, Y is O, R1 is methoxy, ethoxy, cyclopropylmethoxy or 1–2C-alkoxy which is completely or predominantly substituted by fluorine, and R2 and R3, together and including the two carbon atoms to which they are bonded, are a spiro-linked cyclopentane or cyclohexane ring, or a salt thereof.

4. A compound of formula I as claimed in claim 1, in which
from the group of symbols A, B, D and E, independently of one another, one symbol is N (nitrogen), one symbol is C—X and the remaining two symbols are C—H, where X is hydrogen or halogen, Y is O or NH, R1 is methoxy and R2 and R3, together and including the two carbon atoms to which they are bonded, are a spiro-linked cyclopentane or cyclohexane ring, or a salt thereof.

5. A medicament composition useful for treating dermatoses and comprising an effective amount of a compound as claimed in claim 1 and a customary pharmaceutical auxiliary and/or excipient.

6. A method of treating a subject prone to or afflicted with an amenable airway disorder, dermatosis, disorder based on excessive release of TNF and leukotrienes, disorder of the immune system or generalized inflammation in the gastrointestinal area, which comprises administering to such subject an effective amount of a compound as claimed in claim 1.

7. In a method of compounding a medicament composition having an active ingredient for treating an airway disorder by admixing such active ingredient with a customary pharmaceutical auxiliary and/or excipient, the improvement wherein the active ingredient is a compound as claimed in claim 1.

8. In a method of treating a subject afflicted with an amenable dermatosis by administering to such subject an effective amount of active ingredient, the improvement wherein the active ingredient is a compound as claimed in claim 1.

* * * * *

UNITED STATES PATENT AND TRADEMARK OFFICE
CERTIFICATE OF CORRECTION

PATENT NO. : 6,172,074 B1
DATED : January 9, 2001
INVENTOR(S) : Thomas Bär et al.

It is certified that error appears in the above-identified patent and that said Letters Patent is hereby corrected as shown below:

Column 21,
Line 20, "Y is O or NH," should read -- Y is O, --.

Signed and Sealed this

Twenty-fifth Day of September, 2001

*Attest:*

NICHOLAS P. GODICI
*Acting Director of the United States Patent and Trademark Office*

*Attesting Officer*